(12) United States Patent
Flisak et al.

(10) Patent No.: US 6,300,359 B1
(45) Date of Patent: Oct. 9, 2001

(54) (E)-3-[1-N-BUTYL-5-[2-(2-CARBOXYPHENYL) METHOXY-4-CHLOROPHENYL]-1H-PYRAZOL-4-YL]-2-[(5-METHOXY-2,3-DIHYDROBENZOFURAN-6-YL)METHYL]-PROP-2-ENOIC ACID MONOARGININYL SALT

(75) Inventors: Joseph Robert Flisak, Lansdale; Albert Stephen Kearney, Collegeville; Nagesh Palepu, Norristown; Cherng-Yih Perng, Berwyn, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/581,066

(22) PCT Filed: Dec. 7, 1998

(86) PCT No.: PCT/US98/25903
§ 371 Date: Jun. 8, 2000
§ 102(e) Date: Jun. 8, 2000

(87) PCT Pub. No.: WO99/29685
PCT Pub. Date: Jun. 17, 1999

Related U.S. Application Data

(60) Provisional application No. 60/067,732, filed on Dec. 8, 1997.

(51) Int. Cl.$^7$ .................................................. A61K 31/415
(52) U.S. Cl. ........................................ 514/406; 548/364.4
(58) Field of Search ......................... 514/406; 548/364.4

(56) References Cited

FOREIGN PATENT DOCUMENTS

WO 97/04772    2/1997   (WO) .

OTHER PUBLICATIONS

Luengo, et al., "Process of novel pyrroles, pyrazoles and triazoles", WO 9704772 (Feb., 1997), Chemical Abstracts, (Nov., 1997), vol. 75, Abstract No. 126:225306.

*Primary Examiner*—Dwayne C. Jones
(74) *Attorney, Agent, or Firm*—Linda E. Hall; Stephen A. Venetianer; Charles M. Kinzig

(57) ABSTRACT

This invention relates to a new monoargininyl salt form of the endothelin receptor antagonist (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid.

16 Claims, No Drawings

(E)-3-[1-N-BUTYL-5-[2-(2-CARBOXYPHENYL) METHOXY-4-CHLOROPHENYL]-1H-PYRAZOL-4-YL]-2-[(5-METHOXY-2,3-DIHYDROBENZOFURAN-6-YL)METHYL]-PROP-2-ENOIC ACID MONOARGININYL SALT

This application is a 371 of PCT/US98/25903, filed on Dec. 7, 1998, which claims benefit of Provisional Application Ser. No. 60/067,732 filed Dec. 8, 1997.

FIELD OF THE INVENTION

This invention relates to a new monoargininyl salt form of the endothelin receptor antagonist, (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid.

BACKGROUND OF THE INVENTION

The compound, (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid is included within the large generic class of compounds disclosed and claimed in the co-pending PCT application PCT/US 9612581. The compounds are described as existing in either the free acid form or as "pharmaceutically acceptable salts". Example 2 of PCT/US 9612581 gives the method of producing the diacid, (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid. The activity of the compound as an endothelin receptor antagonist is described in PCT/US 9612581.

SUMMARY OF THE INVENTION

The invention comprises the monoargininyl salt of (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid) which surprisingly has been found to have increased bioavailability as compared to the disodium salt or dissolution-enhancing formulations of the diacid i.e., where the surfactant Tween 80 has been incorporated either alone and in combination with the buffering agent N-methylglucamine.

The invention further constitutes pharmaceutical compositions of the monargininyl salt of (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid) and its use as an endothelin receptor antagonist which is useful in the prevention or treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, subarachnoid hemorrhage, cerebrovascular vasospasm, myocardial ischemia, angina, congestive heart failure, unstable angina, coronary vasospasm and myocardial salvage, the sequelae of diabetes including but not limited to: atherosclerosis, diabetic nephropathy, diabetic retinopathy, retinopathy, diabetic macrovascular disease; and as an adjunct in angioplasty for prevention of restenosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compound of this invention is represented by structural Formula (I):

Formula (I)

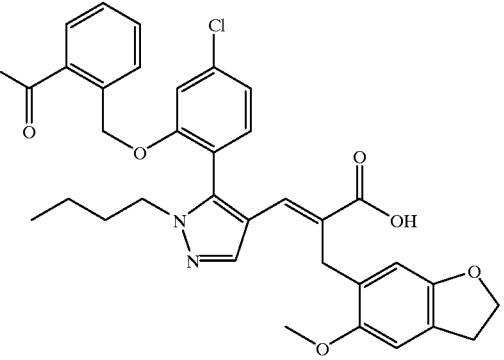

The aqueous solubility of the diacid of the compound of Formula (I) is very limited under acidic conditions. The solubility is less than 0.1 ug/mL at pH<5.34. For compounds possessing a pH-dependent solubility profile of this type, it is not uncommon to find a dissolution-rate limiting component to the oral bioavailability. For the diacid of Formula (I), this contention is supported by the finding that the oral bioavailability in dogs, following the intraduodenal dosing of a non-aqueous solution of a compound of Formula (I) diacid, was approximately 15% which is close to the theoretical maximum value of 18% (the enterohepatic extraction ratio is 0.82). In contrast, the oral bioavailability in dogs, following the oral dosing of a simple capsule formulation of the diacid of Formula (I), was only 3.9%. In an attempt to overcome any dissolution-rate limitation and hence enhance the oral bioavailability, alternate salt forms were studied.

It has now unexpectedly been found that the newly prepared monoargininyl salt of Formula (I) has increased bioavailability as compared to the disodium salt or dissolution-enhancing formulations of the diacid i.e., where the surfactant Tween 80 has been incorporated either alone and in combination with the buffering agent N-methylglucamine. The mean percent oral bioavailability was 13.3% which is comparable to the intraduodenal dosing of a non-aqueous solution of the disodium form. Comparative data for the bioavailability studies is found in Table 1.

TABLE 1

Bioavailability Studies Conducted in Dogs Using Formulation Approaches and Salt Formd of Formula (I)

| Form Dosed | Formulation Dosed | Mean % Oral Bioavailability ± SD |
|---|---|---|
| Disodium Salt | Non-Aqueous Solution[a] | 14.5[b] |
| Diacid | Capsule[c] | 3.9 ± 0.5 |
| Diacid | Capsule with 0.5% Tween 80[d] | 2.3 ± 3.7 |
| Diacid | Capsule with 0.5% Tween 80 & 2 MEq NMG[d] | 6.3 ± 5.3 |
| Disodium Salt | Capsule[c] | 6.2 ± 4.1 |
| Monoargininyl Salt | Capsule[c] | 13.8 ± 7.6 |

[a]Solution contained 99% PEG 400 and 1% DMSO and was dosed intraduodenally.
[b]Dosed in only 2 animals.
[c]Formulations also contain microcrystalline cellulose as a diluent.
[d]Formulations also contained some microcrystalline cellulose, lactose, and starch.

As shown in Table 2, the monoarginine salt was minimally hygroscopic absorbing only 2.3% moisture over a relative humidity range of 0 to 90%. It was slightly more hygroscopic than the diacid form and considerably less hygroscopic than the amorphous disodium salt form. Accelerated stability studies, performed on the monoarginine salt, show that it is chemically stable for at least three weeks when stored at 50° C.

TABLE 2

Hygroscopicity Studies for the Diacid and the Disodium and Monoargininyl Salt Forms of Formula (I)

| % Relative Humidity | % Moisture Uptake at 250Ca | | |
|---|---|---|---|
| | Diacid | Disodium | Monoarginine |
| 0 | 0 | 0 | 0 |
| 10 | 0.077 | 1.849 | 0.261 |
| 20 | 0.088 | 2.838 | 0.382 |
| 30 | 0.126 | 3.821 | 0.526 |
| 40 | 0.184 | 5.013 | 0.689 |
| 50 | 0.245 | 6.773 | 0.827 |
| 60 | 0.316 | 10.188 | 0.982 |
| 70 | 0.395 | 15.919 | 1.092 |
| 80 | 0.509 | 22.472 | 1.434 |
| 90 | 0.518 | 33.671 | 2.334 |

[a]Measured on a dynamic vapor sorption analyzer as percentage weight gain in the sample.

Pharmaceutical compositions having endothelin receptor antagonist activity which comprises a pharmaceutical carrier containing and active but non-toxic quantity of the monoargininyl salt of a compound of Formula (I) are also objects of this invention.

In order to use the monoargininyl salt of a compound of the Formula (I) for the treatment of humans and other mammals it is normally formulated in accordance with standard pharmaceutical practice as a pharmaceutical composition.

The monoargininyl salt of Formula (I) may be administered in a standard manner for the treatment of the indicated diseases, for example orally, parenterally, sub-lingually, transdermally, rectally, via inhalation, via ocular administration, or via buccal administration.

The monoargininyl salt of Formula (I) when given orally can be formulated as a syrup, tablet, capsule and lozenge. A syrup formulation will generally consist of a suspension or solution of the compound in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, cellulose, mannitol, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises the monoargininyl salt of Formula (I), with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical ophthalmic formulations are isotonic solutions buffered to neutral pH in the range of 6.5 to 7.8, for example a citrate buffer made isotonic with sodium chloride.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of the monoargininyl salt of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of the monoargininyl salt of a compound of Formula (I).

The daily dosage regimen for oral administration is suitably about 0.01 mg/Kg to 40 mg/Kg, of the monoargininyl salt of Formula (I) or a pharmaceutically acceptable salt thereof calculated as the free acid. The daily dosage regimen for parenteral administration is suitably about 0.001 mg/Kg to 40 mg/Kg, of the monoargininyl salt of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when the compound of the invention is administered in accordance with the present invention.

The biological activity of the monoargininyl salt of Formula (I) is demonstrated by the following test:

Bioavailability Study

Four male beagle dogs (approximate weight; 10–15 kg) were used. The study was conducted as a crossover design on three separate study days, and the animals were allowed to recover for one week between each leg of the experiment. A CBC screen was performed on the animals before each study day to obtain baseline values and assure hematological recovery. On each study day, a catheter was placed in a cephalic vein for blood sampling. On study day three a catheter was also placed in a saphenous vein for i.v. administration. The animals were fasted overnight prior to treatment, and food was prepared after taking the 240 min blood samples. On study days one and two (oral dosing), the dogs were restrained in slings for approximately 1 hour and then transferred to metabolism cages. On study day three, the dogs were restrained in slings for approximately 2 hours during the study and then transferred to metabolism cages. The animals were housed in individual cages in unidirectional air flow rooms with controlled temperature (22±2° C.) and relative humidity (50±10%) and 12 h light/dark cycles (0600–1800). The dogs were acclimatized for at least 5 days prior to the experiment and provided food, except for the overnight period prior to dosing. Filtered tap water was supplied ad libitum.

The animals were fasted overnight prior to administration of the compound. Food was provided after drawing the 240 min blood samples.

Preparation of Dose Solutions and Dosing Procedures

For the first oral administration, solid monoarginyl salt of Formula (I) was triturated by glass mortar and pestle to obtain a uniform particle size. The compound and Avicel PH 102 was mixed as a 50:50 ratio and packed into a white opaque gelatin capsule (size 00).

For the second oral administration, solid di-acid of Formula (I) was triturated by lass mortar and pestle to obtain a uniform particle size. The compound and Avicel PH 102 was mixed as a 50:50 ratio and packed into a white opaque gelatin capsule (size 00).

The dose solution for i.v. administration will be prepared in injectable saline Solution containing less than 3% ethanol.

On study day one, two animals received the monoargininyl salt of Formula (I)(16.2 umol [10 mg]/kg target dose) in a gelatin capsule, and the other two animals received the di-acid of Formula (I)(16.2 umol [10 mg]kg target dose) in a gelatin capsule.

On study day two, the same formulations were used, but the study animals were crossed over to receive the opposite formulation that they were given on day 1.

On study day three, the dogs received a compound of Formula (I) (0.5 mg/mL in injectable saline) as a 90 min intravenous infusion (2.43 umol [1.5 mg]/kg target dose, 2 mL/kg/h, 3 mL/kg total volume).

Blood Sample Collection

Blood samples (approximately 0.25 mL) were collected into 1 mL syringes from the cephalic vein catheter at the approximate times and volumes shown in the tables below and transferred into heparinized 1.5 mL Eppendorf tubes. Plasma (50 uL) was isolated from the blood samples by centrifugation, transferred to new Eppendorf tubes and quick frozen on dry ice. Extra plasma was also frozen and saved. All samples were stored at or about −70° C. until analyzed.

| Approximate Sample Times Following Oral Administration | | | | | | | | | | | | | | | |
|---|---|---|---|---|---|---|---|---|---|---|---|---|---|---|---|
| Time (min) | 0 | 5 | 15 | 30 | 45 | 60 | 90 | 120 | 180 | 240 | 360 | 480 | 600 | 720 | 1440 |

Total blood withdrawn: Approximately 11.5 mL (includes pre-draw)

Approximate Sample Times Following Initiation of Intravenous Infusion

| Time (min) | 0 | 15 | 30 | 45 | 60 | 75 | 90 | 92 | 95 | 105 | 120 | 180 | 240 | 360 | 480 | 600 | 720 | 1440 |
|---|---|---|---|---|---|---|---|---|---|---|---|---|---|---|---|---|---|---|
| | ↑ Start infusion | | | | | | | ↑ End infusion | | | | | | | | | | |

Total blood withdrawn: Approximately 13.5 mL (includes pre-draw)

Concentrations of the compound of Formula (I) in plasma samples were quantified using an HPLC/MS/MS method.

EXAMPLE 1

Preparation of(E)-3-[1-n-Butyl-5-[2-(2-carboxyphenyl)methoxy-4-chlorophenyl]1H-pyrazol-4-yl]-2-[(5-methoxy-2,3-dihydrobenzofuran-6-yl)methyl]-prop-2-enoic Acid, Monoargininyl Salt L-Arginine (152.25 g, 0.87 mole) was added, with stirring, to a mixture of methanol (4 L) and water (40 mL) which had been heated to about 40° C. The temperature was then raised to 50° C. and the suspension was stirred for 15 minutes. SB 247083 (525 g, 0.85 mole) was then added, and the suspension was heated to about 55° C. After all of the solid dissolved, the solution was filtered. The filtrate was stirred and slowly cooled to room temperature. Upon reaching room temperature, the filtrate was stirred for about 1 hour. The resulting crystals were filtered off then washed with about 200 ml of methanol. Then the crystals were air dried for about 30 minutes then vacuum dried at 50 to 60° C.

Sharp endotherm onsets at 214.4 C (delta H=85 J/g) from DSC.

EXAMPLE 2

Preparation of a pharmaceutical composition of (E)-3-[1-n-Butyl-5-[2-(2-carboxyphenyl)methoxy-4-chlorophenyl]-

1H-pyrazol-4-yl]-2-[(5-methoxy-2.3-dihydrobenzofuran-6-yl)methyl]-prop-2-enoic Acid Monoargininyl Salt Formulations for pharmaceutical use incorporating the compound of the present invention can be prepared in various forms and with numerous excipients. Examples of such formulations are given below.

Inhalant Formulation

A compound of Formula (I), (1 mg to 100 mg) is aerosolized from a metered dose inhaler to deliver the desired amount of drug per use.

|   | Ingredients | Amount per Tablet |
|---|---|---|
| 1. | Active ingredient (Cpd of Form. I) | 40.0 mg |
| 2. | Lactose | 40.0 mg |
|   | Microcrystalline Cellulose | 16.0 mg |
| 4. | Sodium Starch Glycolate | 4.0 mg |
| 5. | Povidone | 5.3 mg |
| 6. | Microcrystalline Cellulose | 89.2 mg |
| 7. | Sodium Starch Glycolate | 4.0 mg |
| 8. | Mg Stearate | 1.5 mg |
|   | Total | 200.0 mg |

Procedure for Tablets:

Step 1 Blend ingredients No. 1, 2, 3, 4, and 5 in a suitable mixer/blender.

Step 2 While mixing, add water to the blend to produce a wet mass then continue to granulate until a suitable wet granulation is obtained.

Step 3 Pass the wet mass through a mill fitted with an appropriate screen.

Step 4 Dry the granules in a fluid-bed dryer at an appropriate inlet temperature.

Step 5 Screen the granulate through a mill fitted with an appropriate screen.

Step 6 Blend the granules with ingredients No. 6, 7, and 8.

Step 7 Compress the formulation on an appropriate tablet press.

Parenteral Formulation

A pharmaceutical composition for parenteral administration is prepared by dissolving an appropriate amount of a compound of Formula (I) in polyethylene glycol with heating. This solution is then diluted with water for injections Ph Eur. (to 100 ml). The solution is then steriled by filtration through a 0.22 micron membrane filter and sealed in sterile containers.

What is claimed is:

1. (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl )methyl]-prop-2-enoic acid, monoargininyl salt.

2. A pharmaceutical composition comprising a compound of claim 1 and a pharmaceutically acceptable carrier.

3. A composition according to claim 2 for oral administration.

4. A compound of claim 1 for use as an endothelin receptor antagonist.

5. A method of treatment of diseases caused by an excess of endothelin comprising administering to a subject in need thereof, an effective amount of an endothelin receptor antagonist of claim 1.

6. A method of treating hypertension, renal failure or cerebrovascular disease which comprises administering to a subject in need thereof, an effective amount of a compound of claim 1.

7. A method for the treatment of chronic renal failure which comprises administering to a subject in need thereof, an effective amount of a compound of claim 1.

8. A method of treatment of benign prostatic hypertrophy which comprises administering to a subject in need thereof, an effective amount of a compound of claim 1.

9. A method of treatment of congestive heart failure which comprises administering to a subject in need thereof, an effective amount of a compound of claim 1.

10. A method of treatment of unstable angina, coronary vasospasm and myocardial salvage, which comprises administering to a subject in need thereof an effective amount of a compound of claim 1.

11. A method of preventing or treating restenosis which comprises administering to a subject in need thereof, an effective amount of a compound of claim 1.

12. A method of treatment of pulmonary hypertension which comprises administering to a subject in need thereof, an effective amount of a compound of claim 1.

13. A method of treatment of atherosclerosis which comprises administering to a subject in need thereof, an effective amount of a compound of claim 1.

14. A method of preventing and treating the sequelae of diabetes which comprises administering to a subject in need thereof, an effective amount of a compound of claim 1.

15. A method of treatment of stroke or subarachnoid hemorrhage which comprises administering to a subject in need thereof, an effective amount of a compound of claim 1.

16. A process for preparing a compound of claim 1 by adding L-Arginine to (E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid.

* * * * *